United States Patent [19]

Mertens et al.

[11] Patent Number: 4,847,251

[45] Date of Patent: Jul. 11, 1989

[54] PYRIDAZINONE DERIVATIVES, AND PHARMACEUTICAL COMPOSITIONS CONTAINING THEM

[75] Inventors: Alfred Mertens, Schriesheim; Wolfgang Von Der Saal, Weinheim; Bernd Müller-Beckmann, Grünstadt; Gisbert Sponer, Laudenbach, all of Fed. Rep. of Germany

[73] Assignee: Boehringer Mannheim GmbH, Mannheim, Fed. Rep. of Germany

[21] Appl. No.: 80,998

[22] Filed: Aug. 3, 1987

[30] Foreign Application Priority Data

Aug. 8, 1986 [DE] Fed. Rep. of Germany ....... 3626865

[51] Int. Cl.[4] .................. A61K 31/50; A61K 31/505; A61K 31/53; C07D 401/04
[52] U.S. Cl. ..................................... 514/247; 544/180; 544/295; 544/194; 544/219; 544/237; 544/238; 514/241; 514/245; 514/248; 514/249; 514/252; 514/253; 514/254
[58] Field of Search ............... 544/295, 219, 238, 237, 544/180, 194; 514/247, 241, 245, 248, 249, 252, 253, 254

[56] References Cited

U.S. PATENT DOCUMENTS

4,643,998  2/1987  Hilboll et al. .................. 544/238
4,667,033  5/1987  Hilboll et al. .................. 544/238
4,783,463  11/1988  Kuhla et al. .................. 514/252

OTHER PUBLICATIONS

Hauel et al., Chemical Abstracts Entry 106:18589r (1987) of German Offen 3,511,110 published Oct. 2, 1968.
International Application Published Under the Patent Cooperation Treaty WO 87/02587, International Publication Date: 7 May 1987.

Primary Examiner—John M. Ford
Attorney, Agent, or Firm—Armstrong, Nidaido, Marmelstein, Kubovcik & Murray

[57] ABSTRACT

The present invention provides pyridazinone derivatives of the general formula:

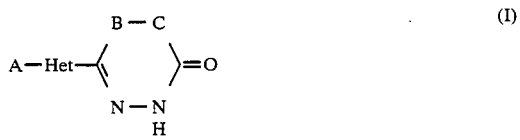

wherein Het is a mono- or bicyclic heterocycle with one or two nitrogen atoms, B-C is a —$CHR_1$—$CH_2$—, —$CR_1$=CH—, —$CHR_1$—O—, —O—$CHR_1$—, —$CHR_1$—NH— or —NH—$CHR_1$— group, $R_1$ being a hydrogen atom or an alkyl radical, and A is an amino, alkylcarbonylamino, aminocarbonylamino, aminothiocarbonylamino, alkylaminothiocarbonylamino, alkylamionocarbonylamino, N'-cyanoguanidino or N'-cyano-N''-alkylguanidino group, a substituted phenyl ring or heterocycle attached via a nitrogen or sulphur atom, or a mono- or bicyclic substituted heterocycle with 1 to 3 nitrogen atoms, one ring nitrogen atom being directly attached to Het; as well as the physiologically acceptable salts thereof.

The present invention also provides processes for the preparation of these pyridazinone drivatives and pharmaceutical compositions containing them for the treatment of heart and circulatory diseases.

21 Claims, No Drawings

PYRIDAZINONE DERIVATIVES, AND PHARMACEUTICAL COMPOSITIONS CONTAINING THEM

The present invention is concerned with new pyridazinone derivatives, processes for the preparation thereof and pharmaceutical compositions containing them.

The new pyridazinone derivatives according to the present invention are compounds of the general formula:

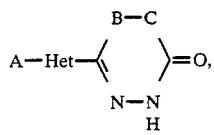

wherein Het is a mono- or bicyclic heterocycle with one or two nitrogen atoms, B-C is a $-CHR_1-CH_2-$, $-CR_1=CH-$, $-CHR_1-O-$, $-O-CHR_1-$, $-CHR_1-NH-$ or $-NH-CHR_1$ group, $R_1$ being a hydrogen atom or an alkyl radical, and A is an amino, alkylcarbonylamino, aminocarbonylamino, aminothiocarbonylamino, alkylaminothiocarbonylamino alkylaminocarbonylamino, N'-cyanoguanidino or N'-cyano-N''-alkylguanidino group, a substituted phenyl ring or heterocycle attached via a nitrogen or sulphur atom, or a mono- or bicyclic, substituted heterocycle containing 1 to 3 nitrogen atoms, one ring nitrogen atom being attached directly to Het; as well as the physiologically acceptable salts thereof.

If the compounds of general formula (I) contain an asymmetric carbon, the present invention also includes the optically-active forms and the racemic mixtures of these compounds.

The new compounds of the present invention display valuable pharmacological properties and, in particular, they increase the strength of the heart and/or lower the blood pressure and/or influence the thrombocyte aggregation and improve the microcirculation.

In general formula (I), Het represents a mono- or bicyclic heterocycle with one or two nitrogen atoms, 6-membered heterocycles thereby being preferred, for example pyridine, pyrazine, pyrimidine and pyridazine. Preferred bicycles include quinoline, isoquinoline, quinoxaline, quinazoline and phthalazine.

If, in general formula (I), B-C is a $-CHR_1-CH-$, $-CR_1=CH-$, $-CHR_1-O-$, $-O-CHR_1-$, $-CHR_1-NH-$ or $-NH-CHR_1-$ group, then there are preferred the $-CHR_1-CH_2-$, $-CR_1=CH-$, $-CHR_1-O-$ and $-CHR_1-NH-$ groups, $R_1$ in these groups being a hydrogen atom or an alkyl radical containing 1 to 3 carbon atoms.

If A in general formula (I) is an amino, alkylcarbonylamino, aminocarbonylamino, aminothiocarbonylamino, alkylaminothiocarbonylamino, alkylaminocarbonylamino, N'-cyanoguanidino or N'-cyano-N''-alkylguanidino radical, then A is preferably an amino, alkylcarbonylamino, alkylaminocarbonylamino or N'-cyano-N''-alkyl-guanidino group, the alkyl moieties of the above-mentioned groups containing up to 5 carbon atoms, as well as an aminocarbonylamino and aminothiocarbonylamino group.

If A in general formula (I) is a substituted phenyl ring or heterocycle attached via a nitrogen or sulphur atom, then A is, in this case, preferably a phenylamino, pyridylamino, thiazoleamino, tetrazoleamino, phenylthio, pyridylthio, thiazolethio, triazolethio or tetrazolethio radical, a phenyl ring or a heterocycle containing one or more substitutents selected from $C_1-C_6$-alkyl, $C_1-C_6$-alkoxy, hydroxyl, nitro or halogen, preferably fluorine, chlorine or bromine.

If A in general formula (I) signifies a mono- or becyclic substituted heterocycle containing 1 to 3 nitrogen atoms, the ring nitrogen being attached directly to Het, then there are preferred five-membered rings with 1 to 3 nitrogen atoms, six-membered rings with 1 to 3 nitrogen atoms and bicyclic heterocycles with 1 or 2 nitrogen atoms, the above-mentioned heterocycles optionally being substituted by one or more alkyl, alkoxy, hydroxyl, alkylcarbonyl or alkylcarbonylamino radicals and the above-mentioned alkyl moieties containing up to 6 carbon atoms.

Especially preferred compounds of general formula (I) are those in which Het is a pyridine, pyrazine, pyrimidine, pyridazine or phthalazine ring, B-C is a $-CHR_1-CH_2-$, $-CR_1=CH-$, $-CHR_1-O-$ or $-CHR_1-NH-$ group, $R_1$ in the above-mentioned groups being a hydrogen atom or a methyl radical, and A is an alkylcarbonylamino, alkylaminocarbonylamino or N'-cyano-N''-alkylguanidino radical, the alkyl moieties containing up to 3 carbon atoms, or an aminocarbonylamino or aminothiocarbonylamino group, or A is an amino, phenylamino, pyridylamino, thiazoleamino, tetrazoleamino or triazolethio radical, the phenyl ring or the heterocycles optionally being subsstituted by one or more methyl, methoxy, hydroxyl or chlorine resideues, or A is a monocyclic five-membered ring containing 1 to 3 nitrogen atoms, there being preferred the pyrrole, pyrazole, imidazole, imidazoline and triazole rings, or A is a monocyclic six-membered ring containing 1 to 3 nitrogen atoms, there being preferred the piperidine, piperazine and triazine rings, or A is a bicyclic heterocycle, the benzimidazole and 4,5,6,7-tetrahydrobenzimidazole rings being especially preferred. Especially preferred substituents for the above-mentioned five- and six-membered rings and for the bicyclic heterocycles are methyl, hydroxyl, methylcarbonyl and methylcarbonylamino.

The new compounds of general formula (I) according to the present invention can be prepared in known manner:

(a) a γ-ketocarboxylic acid of the general formula:

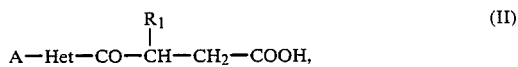

in which A, Het and $R_1$ have the above-given meanings and B-C is a $-CHR_1-CH_2-$ group, is cyclised with hydrazine and, if desired, the compound of general formula (I) thus obtained is converted by oxidation inot another compound of general formula (I), in which A, Het and $R_1$ have the above-given meanings and B-C is a $-CR_1=CH-$ group; or (b) a hydrazone of the general formula:

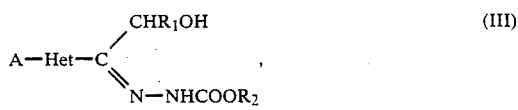

in which A, Het and $R_1$ have the above-given meanings and $R_2$ is a lower alkyl radical, for example a methyl or ethyl radical, is cyclised to a compound of general formula (I), in which A, Het and $R_1$ have the above-given meanings and B-C is a —$CHR_1$—O— group; or (c) a hydrazide of the general formula:

(IV)

in which A and Het have the above-given meanings, is cyclised with an acid of the general formula:

Hal—$CHR_1$—COOH     (V), in which $R_1$ has the above-given meaning and Hal is a halogen atom, or with a reactive derivative of the acid to give a compound of general formula (I), in which A, Het and $R_1$ have the above-given meanings and B-C is a —O—$CHR_1$— group; or (d) an imino ether of the general formula:

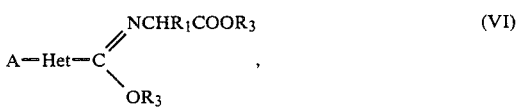
(VI)

in which A, Het and $R_1$ have the above-given meanings and the two substitutents $R_3$ are the same or different and are alkyl radicals containing up to 4 carbon atoms, is cyclised with hydrazine to give a compound of general formula (I), in which A, Het and $R_1$ have the above-given meanings and B-C is an —NH—$CHR_1$— group; or (e) a compound of the general formula:

A—Het—$COCHR_1NHCOOR_4$     (VII), in which A, Het and $R_1$ have the above-given meanings and $R_4$ is an alkyl radical containing up to 4 carbon atoms, is cyclised with hydrazine to give a compound of general formula (I), in which A, Het and $R_1$ have the above-given meanings and B-C is a —$CHR_1$—NH— group.

In the case of the reactions described in processes (a), (d) and (e) of compounds of general formulae (II), (VI) and (VII) with hydrazine, it is preferable to work in a solvent, for example water or and alcohol, at a temperature of from 0° C. to the boiling point of the solvent used.

The oxidation of 4,5-dihydro-3(2H)-pyridazinone to 3(2H)pyridazinone, also described in process (a), takes place by processes known from the literature, such as bromination/dehydrobromination, dehydrogenation catalysed by noble metal caralysts or oxidation/reduction processes with manganese dioxide or m-nitrobenzenesulphonic acid as reagents (see J. Med. Chem., 17, 273/1974).

The cyclisation described in process (b) of compounds of general formula (III) is advantageously carried out in the presence of a base, for example sodium hydroxide or sodium alcoholate, in a solvent, such as water or an alcohol, at a temperature of from 0° C. to the boiling point of the solvent used.

The cyclisation described in process (c) of compounds of general formula (IV) with halocarboxylic acids or reactive derivatives of the acids is preferable carried out in two steps, wherein a halocarboxylic acid halide is advantageously first reacted with the hydrazide. The reaction is carried out in an inert solvent, for example toluene, methylene chloride or pyridine, optionally with the addition of a base, for example potassium carbonate or triethylamine, at a temperature of from 0° to 100° C. The diacylhydrazine thus obtained is cyclised in a second step with a base, for example sodim hydride or an alkali metal carbonate, in a solvent, for example dimethylformamide or acetone, at an elevated temperature of from 40° to 150° C.

If, according to the above-described processes, compounds of general formula (I) are obtained in which A is an amino group, these compounds can subsequently be converted into other compounds of general formula (I) in which A has the above-given definition. These conversions can take place, for example, by acylation or by the addition of isocyanates, isothiocyanates or carbonyldiimides, compounds of general formula (I) being obtained in which A is an alkylcarbonylamino, aminocarbonylamino, aminothiocarbonylamino, alkylaminothiocarbonylamino, alkylaminocarbonylamino, N'-cyanoguanidino or N'-cyano-N''-alkylguanidino group.

Furthermore, compounds obtained of general formula (I) can subsequently, if desired, be converted into the physiologically acceptable acid-addition salts thereof with inorganic and organic acids. As acids for this purpose, there can be used, for example, hydrochloric acid, hydrobromic acid, sulphuric acid, phosphoric acid, fumaric acid, succinic acid, tartaric acid, citric acid, lactic acid, maleic acid or methanesulphonic acid.

As already mentioned initially, the new compounds of general formula (I), the tautomers and the physiologically acceptable salts thereof display, in the case of a long period of action, superior pharmacological properties, especially blood pressure-lowering and/or positive inotropic action and/or influence the thrombocyte function and improve the microcirculation.

The inotropic activity of certain compounds of the present invention was determined according to the procedure described below. Male Sprague-Dawley rats weighing between 350 and 450 g were narcotized by intraperitoneal injection of a barbiturate and fitted with instrumentation for the examinations as follows:

A pressure measuring carheter (Miller Mikrotip/-diameter 0.5 mm) was inserted through the arteria carotis dextra into the left ventricle. The pressure inside the left ventricle was continually registered through this carheter. The signal from this Mikrotip was electronically differentiated and $(dp/dt)_{60}$- the slope of the pressure-time curve at a pressure of 60 mmHg - was taken as a measure for the inotropy.

A polypropylene carheter was bound in a vena jugularis for the intravenous injection of the test substances.

A further polypropylene carheter was inserted through an arteria femoralis into the abdominal aorta for the direct measurement of the arterial blood pressure.

The ECG was traced with subcutaneous insertion electrodes.

During the preparation of the animal and during the entire test period the rats were fixed on an electronically heated and thermostatically controlled operating table.

The test substances were always introduced by intravenous injection, with an injection volume, per injection, of 1 ml/kg body weight. In intervals of 10 min each, doses increasing from 0.01 to 30 mg of the test substances were intravenously injected. In this way dose effect curves for the measured parameters for the investigated substances were obtained.

From the measured data, using a regression calculation, equipotent doses for the positively inotropic effect $(dp/dt)_{60}$ of the substances, the maximum effect obtained (maximal increase of $(dp/dt)_{60}$) and its corresponding dose were determined. The table that follows reports the equipotent doses ($ED_{1,5}$ = the dose in mg/kg that leads to an increase of $(dp/dt)_{60}$ of 1.5 mHg/sec) and the maximal effectiveness ($w_{max}$ = the maximal increase of $(dp/dt)_{60}$) and the dose producing the maximum effectiveness.

| Substance from Exp. | $ED_{1,5}$ mHg/sec [mg/kg i. v.] | $W_{max}$ [mHg/sec] | [mg/kg i. v.] |
|---|---|---|---|
| Example 1 | 0,033 | 2,4 | 0,1 |
| Example 6 | 0,78 | 1,8 | 1,0 |
| Example 10 | 0,64 | 2,3 | 1,0 |

For the preparation of pharmaceutical compositions, the compounds of general formula (I) are mixed in known manner with appropriate pharmaceutical carrier materials, aroma, flavouring and colouring materials and formed, for example, into tablets or dragees or, with the addition of appropriate adjuvants, are suspended or dissolved in water or an oil, for example olive oil.

The new compounds of general formula (I) according to the present invention and the salts thereof can be administered enterally or parenterally in liquid or solid form. As injection medium, it is preferred to use water which contains the additives usual in the case of injection solutions, for example stabilising agents, solubilising agents or buffers.

Additives of this kind include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The new compounds according to the present invention are usually administered in amounts of from 1 to 50 mg. per day, referred to a body weight of 75 kg. It is preferred to administer, 2 to 3 times a day, 1 to 2 tablets with a content of active material of 0.5 to 20 mg. The tablets can also be retarded, in which case only 1 to 2 tablets with 1 to 50 mg. of active material have to be given once per day. The active material can also be administered by injection 1 to 8 times a day or by continuous infusion, in which case amounts of from 0.5 to 20 mg. per day normally suffice.

Preferred in the meaning of the present invention are, apart from the compounds mentioned in the following Examples, the following compounds and the tautomers thereof:

4,5-dihydro-6-[5-(1H-pyrrol-1-yl)-2-pyridyl]-3(2H)-pyridazinone
4,5-dihydro-6-[2-(1H-pyrrol-1-yl)-6-pyridyl]-3(2H)-pyridazinone
4,5-dihydro-3-[2-(1H-imidazol-1-yl)-5-pyridyl]-6(1H)-1,2,4-triazinone
2-[2-(1H-imidazol-1-yl)-5(4H,6H)-1,3,4-oxadiazinone
4,5-dihydro-5-methyl-6-[2-(1-H-pyrazol-1-yl)-5-pyrimidinyl]-3(2H)-pyridazinone
4,5-dihydro-5-methyl-6-[3-(1H-pyrazol-1-yl)-6-pyridazinyl]-3(2H)-pyridazinone
4,5-dihydro-5-methyl-6-[2-(2-oxo-imidazolidin-1-yl)-5-pyrazinyl]-3(2H)-pyridazinone
4,5-dihydro-6-[2-(1H-1,2,4-triazol-1-yl)-3-pyridyl]-3(2H)-pyridazinone
4,5-dihydro-6-[2-(4H-1,2,4-triazol-4-yl)-3-pyridyl]-3(2H)-pyridazinone
4,5-dihydro-5-methyl-6-[2(1,2,3,4,5,6-hexahydro-2,4,6-trioxo-1,3,5-triazin-1-yl)-4-pyridyl]-3(2H)-pyridazinone 4,5-dihydro-5-methyl-6-[2-(1H-benzimidazol-1-yl)-5-pyrimidinyl]-3(2H)-pyridazinone
4,5-dihydro-5-methyl-6-[2-(4,5,6,7-tetrahydro-1H-benzimidazol-1-yl)-5-pyrimidinyl]-3(2H)-piridazinone
4,5-dihydro-3[1-(1H-imidazol-1-yl)-4-phthalazinyl]-6(1H)-1,2,4-triazinone
2-[1-(1H-imidazol-1-yl)-4-phthalazinyl]-5(4H,6H)-1,3,4-oxadiazinone
4,5-dihydro-6-[2-(acetylamino)-5-pyridyl]-3(2H)-pyridazinone
6-[2-(aminocarbonylamino)-5-pyridyl]-3(2H)-pyridazinone 5-methyl-6-[2-(methylaminocarbonylamino)-5-pyridyl]-3(2H)-pyridazinone
4,5-dihydro-6-[2-methylaminothiocarbonylamino)-5-pyridyl]-3(2H)-1,2,4-triazinone
5-[2-(N'-cyano-N''-methylguanidino)-5-pyridyl]-2(3H,6H)-1,3,4-oxadiazinone
4,5-dihydro-6-[2-(phenylamino-6-pyridyl]-3(2H)-pyridazinone
4,5-dihydro-6-[2-(2-thiazolylamino)-6-pyridyl]-3(2H)-pyridazinone
4,5-dihydro-6-[2-(5-tetrazolylamino)-6-pyridyl]-3(2H)-pyridazinone
4,5-dihydro-6-[2-(1,2,4-triazol-5-ylthio)-5-pyridyl]-3(2H)-pyridazinone
6-[2-(4-acetyl-1-piperazinyl)-5-pyridyl]-3(2H)-pyridazinone
4,5-dihydro-5-methyl-6-[2-(4-acetylamino-1-piperazinyl)-5-pyrimidinyl]-3(2H)-pyridazinone
4,5-dihydro-5-methyl-6-[2-(aminocarbonylamino)-5-pyridyl]-3(2H)-pyridazinone
4,5-dihydro-5-methyl-6-[2-(aminothiocarbonylamino)-5-pyridyl]-3(2H)-pyridazinone
4,5-dihydro-5-methyl-6-[2-(N-cyano-N''-methylguanidino)-5-pyridyl]-3(2H)-pyridazinone
4,5-dihydro-5-methyl-6[2-(2-phenylamino-5-pyridyl]-3(2H)-pyridazinone
4,5-dihydro-5-methyl-6-[2-(2-thiazolylamino)-5-pyridyl]-3-(2H)-pyridazinone
4,5-dihydro-5-methyl-6-[2-(5-1H-tetrazolylamino)-5-pyridyl]-3(2H)-pyridazinone
4,5-dihydro-5-methyl-6-[2-(5-1H-tetrazolylthio)-5-pyridyl]-3(2H)-pyridazinone
4,5-dihydro-5-methyl-6-[2-(4-acetyl-1-piperazinyl)-5-pyridyl]-3(2H)-pyridazinone
4,5-dihydro-5-methyl-6-[2-(4-acetylamino-1-piperidinyl)-5-pyridyl]-3(2H)-pytidazinone
4,5-dihydro-5-methyl-6-[2-(1-pyrazolyl)-5-pyridyl]-3(2H)-pyridazinone
4,5-dihydro-5-methyl-6-[2-(2-oxo-1-imidazolidinyl)-5-pyridyl]-3(2He-pyridazinone 4,5-dihydro-5-methyl-6-[2-(4H-1,2,4-triazol-4-yl)-5-pyridyl]-3(2H)-pyridazinone 4,5-dihydro-5-methyl-6-[2-(1H-imidazol-1-yl)-4-pyridyl]-3(2H)-pyridazinone 4,5-dihydro-5-methyl-6-[2-(1H-imidazol-1-yl)-6-pyridyl]-3(2H)-pyridazinone 4,5-dihydro-5-methyl-6-[2-(1H-imidazol-1-yl)-3-pyridyl]-3(2H)-pyridazinone 4,5-dihydro-5-methyl-6-[2-(1H-imidazol-1-yl)-5-pyrimidinyl]-3(2H)-pyridazinone 5-[2-(1H-imidazol-1-yl)-5-pyridyl]-2(3H,6H)-1,3,4-oxadiazinone 4,5-dihydro-6-[2-(1H-imidazol-1-yl)-5-pyridyl]-3(2H)-1,2,4-triazinone The following Examples are given for the purpose of illustrating the present invention:

EXAMPLE 1

4,5-Dihydro-5-methyl-6-[2-(1H-imidazol-1-yl)-5-pyridyl]-3(2H)-pyridazinone 10.8 g (40 mmole) 2-[2-(1H-imidazol-1-yl)-5-pyridyl]-2-(4-morpholino)-acetonitrile were added to 1.73 g. sodium hydride (50%) dispersion in mineral oil) in 130 ml. anhydrous tetrahydrofuran and 3.24 ml. (40 mmole) crotonic acid nitrile added dropwise thereto at 25° C. After 2 hours, the reaction mixture was distilled to dryness, the residue was suspended in water and, after acidification with hydrochloric acid to pH 3, extracted twice with dichloromethane. The aqueous phase was adjusted with ammonia to pH 8.5 and extracted three times with dichloromethane. The organic phases were washed with water, dried over anhydrous sodium sulphate and the solvent evaporated off. There were obtained 12.8 g. 2-(4-morpholino)-2-[2-(1-imidazol-1-yl)-5-pyridyl]-3-methylglutaric acid dinitrile as crude product.

10.5 g. of this crude product were heated for 1 hour to 100° C. with 55 ml. 6N hydrochloric acid. The reaction mixture was distilled to dryness in a vacuum and the residue was heated with 200 ml. ethanol and filtered off with suction. The ethanolic filtrate, which contained, as crude product, 3-methyl-4-oxo-4-[2-(1H-imidazol-1-yl)-5-pyridyl]-butyric acid, was mixed with 15 ml. 85% hydrazine hydrate solution and heated to 100° C. for 2.5 hours. The residue obtained by evaporation was worked up with water, filtered off with suction, again suspended in water, adjusted to pH 7 with ammonia and filtered off with suction. After recrystallisation from methanol, there were obtained 4.3 g. (53% of theory) of the title compound; m.p. 217°–219° C.

The starting material can be prepared as follows: (a) 12.2 g. (180 mmole) imidazole, 24.75 g. (180 mmole) potassium carbonate, 20 g. (144 mmole) 2-chloro-5-cyanopyridine and 350 ml. dimethyl sulphoxide were mixed together and stirred for 8 hours under an atmosphere of nitrogen at 70° C. Subsequently, the reaction mixture was distilled to dryness under a high vacuum, the residue was suspended in water, acidified with 2N hydrochloric acid and the precipitate brought into solution by the addition of water. The filtrate was shaken out twice with dichloromethane, the aqueous phase was freed from adhering dichloromethane, adjusted with 2N ammonia solution to pH 8.5 and filtered off with suction. There were obtained 23 g. (93.4% of theory) 2-(1H-imidazol-1-yl)-5-cyanopyridine; m.p. 168°–170° C. (b) 11.5 g. (67.6 mmole) of the above product, 11.5 g. nickel/aluminium powder, 41.4 ml. 100% formic acid and 15.1 ml. water were mixed together and heated to 70° C. for 20 hours under an atmosphere of nitrogen. Subsequently, the reaction mixture was filtered off while still warm, then washed with 90% formic acid and the filtrate was neutralised with ammonia while cooling with ice and filtered off with suction. There were obtained 9.6 g. (82% of theory) 2-(1H-imidazol-1-yl)-pyridin-5-aldehyde; m.p. 133° C. (c) 9.5 g. (54.9 mmole) of the above aldehyde were mixed with 10.45 g. (54.9 mmole) p-toluenesulphonic acid, 6.42 g. (73.7 mmole) morpholine and 57 ml. dioxan. A solution of 3.61 g. (55.4 mmole) potassium cyanide in 3.3 ml. water was added dropwise thereto under an atmosphere of nitrogen and subsequently stirred for 3.5 hours at 110° C. The reaction mixture was considerably concentrated, worked up with a saturated aqueous solution of potassium carbonate and, after the addition of a little water, extracted with dichloromethane. The combined organic phases were washed with water, dried and evaporated. The residue was recrystallised from dichloromethane/diethyl ether with the addition of charcoal. There were obtained 11.8 g. (79.5% of theory) 2-[2-(1H-imidazol-1-yl)-5-pyridyl]-2-(4-morpholino)-acetonitrile; m.p. 148°–150° C.

EXAMPLE 2

4,5-Dihydro-6-[2-(1H-imidazol-1-yl)-5-pyridyl]-3(2H)-pyridazinone 9.5 g. (35.3 mmole) 2-[2-(1H-imidazol-1-yl)-5-pyridyl]-2-(4-morpholino)-acetonitrile were suspended in 105 ml. anhydrous tetrahydrofuran, 7.4 ml. 30% methanolic potassium hydroxide solution were added thereto and subsequently 2.55 ml. (38.5 mmole) acrylonitrile were added dropwise. After 3 hours, the tetrahydrofuran was distilled off, the residue was mixed with water and dichloromethane, acidified with glacial acetic acid and the product extracted three times with dichloromethane. The organic phase was washed twice with water, dried and evaporated. The residue was dissolved in dichloromethane, mixed with diethyl ether and the crystals obtained filtered off with suction. There were obtained 10.3 g. 2-(4-morpholino)-2-(1H-imidazol-1-yl)-5-pyridyl]-glutaric acid dinitrile; m.p. 154°–156° C.

10 g. (31 mmole) of the above dinitrile were boiled for 1.5 hours with 6N hydrochloric acid, subsequently evaporated and the residue boiled with ethanol. After cooling, insoluble material was separated off. The filtrate was mixed with hydrazine hydrate until an alkaline reaction was obtained and boiled under reflux for 3 hours. The evaporation residue was purified on silica gel (elution agent: dichloromethane/methanol 96:4 v/v). There were obtained 4.2 g. of the title compound; m.p. 283°–285° C.

EXAMPLE 3

4,5-Dihydro-5-methyl-6-[2-1H-benzmidazol-1-yl)-5-pyridyl]-3(2H)-pyridazinone

Analogously to Example 2, from 3 g. (9.8 mmole) 2-[2-(1H-benzimidazol-1-yl)-5-pyridyl]-2-(4-morpholino)-acetonitrile and crotonic acid nitrile, after purification on silica gel (elution agent dichloromethane/methanol 99:1 v/v), there were obtained 2.2 g. 2-(4-morpholino)-2-[2-(1H-benzimidazol-1-yl)-5-pyridyl]-3-methylglutaric acid dinitrile as a foamy residue from which, after hydrolysis, reaction with hydrazine hydrate and purification on silica gel (elution agent:

dichloromethane/methanol 35:5 v/v), there was obtained 0.6 g. of the title compound; m.p. 206°-207° C., after recrystallisation from ethanol.

According to the methods described in Example 1 (a) to 1 (c), there were obtained the following intermediates:

(3a) 2-(1H-benzimidazol-1-yl)-5-cyanopyridine; m.p. 193°-195° C.;

(3b) 2-(1H-benzimidazol-1-yl)-pyridine-5-aldehyde; m.p. 148°-150° C.;

(3c) 2-[2-(1H-benzimidazol-1-yl)-5-pyridyl]-2-(4-morpholino)-acetonitrile; m.p. 138°-140° C.

EXAMPLE 4

4,5-Dihydro-5-methyl-6-[2-(4,5,6,7-tetrahydro-1H-benzimidazol-1-yl)-5-pyridyl]-3(2H)-pyridazinone Analogously to Example 2, from 1 g. (3.10 mmole) 2-[2-(4,5,6,7-tetrahydro-1H-benzimidazol-1-yl)-5-pyridyl]-2-(4-morpholino)-acetonitrile and crotonic acid nitrile, after purification on silica gel (elution agent: dichloromethane/methanol 98:2 v/v), there was obtained 0.65 g. 2-(4-morpholino)-2-[2-(4,5,6,7-tetrahydro-1H-benzimidazol-1-yl)-5-pyridyl]-3-methylglutaric acid dinitrile (m.p. 102°-104° C.) from which, after hydrolysis, reaction with hydrazine hydrate and purification on silica gel (elution agent: dichloromethane/methanol 97:3 v/v), there was obtained 0.2 of the title compound; m.p. 234°-235° C., after recrystallisation from ethanol.

According to the methods described in Example 1(a) to 1(c), there were obtained the following intermediates:

4(a) 2-(4,5,6,7-tetrahydro-1H-benzimidazol-1-yl)-5-cyanopyridine; m.p. 197°-200° C.;

4(b) 2-(4,5,6,7-tetrahydro-1H-benzimidazol-1-yl)-pyridine-5-aldehyde; m.p. 84°-88° C.

4(c) 2-[2-(4,5,6,7-tetrahydro-1H-benzimidazol-1-yl)-5-pyridyl]-2-(4-morpholino)-acetonitrile; m.p. 141°-142° C.

EXAMPLE 5

6-[2-(1H-Imidazol-1-yl)-5-pyridyl]-3(2H)-pyridazinone.

2 g. (8.3 mmole) of the compound prepared in Example 2 were boiled in 250 ml. dioxan with 50 g. pyrolusite for 5 hours, filtered off with suction and the filtrate concentrated until it crystallised. After recrystallisation from ethanol, there was obtained 1 g. of the title compound; m.p. 300° C.

In an aqueous manner, from the compounf prepared in Example 1, there was prepared 5-methyl-6-[2-(1H-imidazol-1-yl)-5-pyridyl]-3(2H)-pyridazinone; m.p. 261°-263° C., after recrystallisation from methanol.

EXAMPLE 6

4,5-Dihydro-5-methyl-6-[2-(1H-1,2,4-triazol-1-yl)-5-pyridyl]-3(2H)-pyridazinone

Analogously to Example 2, from 21.7 g. (66.4 mmole) 2-[2-(1H-1,2,4-triazol-1-yl)-5-pyridyl]-2-(4-morpholino)-acetonitrile and crotonic acid nitrile there were obtained 23.1 g. 2-(4-morpholino)-2-[2-(1H-1,2,4-triazol-1-yl)-5-pyridyl]-3-methylglutaric acid dinitrile as a viscous mass from which, after hydrolysis and reaction with hydrazine hydrate, there were obtained 7.4 g. of the title compound; m.p. 256°-257° C., after recrystallisation from 85% ethanol.

According to the methods described in Example 1(a) to 1(c), there were obtained the following intermediates:

6(a) 2-(1H-1,2,4-triazol-1-yl)-5-cyanopyridine; m.p. 210°-212° C.;

6(c) 2-(1H-1,2,4-triazol-1-yl)-pyridine-5-aldehyde; m.p. 163°-166° C.;

6(c) 2-[2-(1H-1,2,4-triazol-1y-yl)-5-pyridyl]-2-(4-morpholino)-acetonitrile; m.p. 167°-171° C.

EXAMPLE 7

4,5-Dihydro-5-methyl-6-[2-(methylaminocarbonylamino)-5-pyridyl]-3(2H)-pyridazinone A mixture of 0.4 g. (2 mmole) 4,5-dihydro-5-methyl-6-(2-amino-5-pyridyl)-3(2H)-pyridazinone, 10 ml. dimethyl sulphoxide and 0.24 ml. (4 mmole) methyl isocyanate was stirred for 16 hours at ambient temperature, evaporated in a vacuum and the residue triturated with water. There were obtained 0.25 g. of the title compound (48% of theory); m.p. 257°-259° C.

The starting material can be prepared as follows: (a) 9.5 g. (80 mmole) 2-amino-5-cyanopyridine (J. Hetercycl. Chem. 11, 397/1974) were reduced analogously to Example 1(b). There were obtained 6.7 g. (69% of theory) 6-aminonicotinaldehyde; m.p. 143°-145° C. (b) By reaction of the above aldehyde with an excess of acetic anhydride under reflux, there was obtained a yield of 55% of theory of N,N-diacetyl-6-aminonicotinaldehyde; m.p. 130°-132° C. (c) Analogously to Example 1(c), from the above diacetyl compound was obtained 2-(2-diacetamido-5-pyridyl)-2-(4-morpholino)-acetonitrile in a yield of 71% of theory; m.p. 116°-118° C. (d) Analogously to Example 1, from the above acetonitrile derivative and crotonic acid nitrile and hydrazine hydrate, with the splitting off of the acetyl group, there was obtained a yield of 69% of theory of 4,5-dihydro-5-methyl-6-(2-amino-5-pyridyl)-3(2H)-pyridazinone; m.p. 210°-211° C.

EXAMPLE 8

4,5-Dihydro-5-methyl-6-[2-acetylamino)-5-pyridyl]-3(2H)-pyridazinone

To a solution of 0.6 g. (3 mmole) 4,5-dihydro-5-methyl-6-(2-amino-5-pyridyl)-3(2H)-pyridazinone in 35 ml. methanol were added dropwise 3.4 ml. acetic anhydride. The reaction mixture was stirred for 2 hours at ambient temperature, filtered and the precipitate obtained recrystallised from methanol. There was obtained 0.2 g. of the title compound (27% of theory); m.p. 230°-232° C.

EXAMPLE 9

4,5-Dihydro-5-methyl-6-[2-(1-pyrrolyl)-5-pyridyl]-3(2H)-pyridazinone

A mixture of 1.0 g. (5 mmole) 4,5-dihydro-5-methyl-6-(2-amino-5-pyridyl)-3(2H)-pyridazinone, 0.66 g. (5 mmole) 2,5-dimethoxytetrahydrofuran and 15 ml. acetic acid was heated under reflux for 30 minutes. The reaction mixture was evaporated, the residue was taken up in dichloromethane, washes with an aqueous solution of sodium hydrogen carbonate, evaporated and the residue chromatographed on silica gel (elution agent: trichloromethane/methanol 19:1 v/v). There were obained 0.5 g. of the title compound (39% of theory); m.p. 192°-193° C., after recrystallisation from diethyl ether.

EXAMPLE 10

4,5-Dihydro-5-methyl-6-[2-(phenylamino)-5-pyridyl]-3(2H)-pyridazinone

Analogously to Example 1, from 1.65 g. (5.6 mmole) 2-[2-(phenylamino)-5-pyridyl]-2-(4-morpholino)-acetonitrile and crotonic acid nitrile, after purification on silica gel (elution agent: dichloromethane/methanol, 99:1 v/v), there was obtained 1.6 g. 2-(4-morpholino)-2-[2-(phenylamino)-5-pyridyl]-3-methylglutaric acid dinitrile as a foamy residue from which, after hydrolysis, reaction with hydrazine hydrate and purification on silica gel (elution agent: dichloromethane/methanol, 97:3 v/v), there was obtained 0.6 g. of the title compound; m.p. 202°–204° C., after recrystallisation from ethanol.

According to the methods described in Example 1(a) to 1(c), there were obtained the following intermediates:

10(a) 2-phenylamino-5-cyanopyridine; m.p. 180°–181° C.
10(b) 2-phenylaminopyridine-5-aldehyde; m.p. 148°–150° C.
10(c) 2-(2-phenylamino-5-pyridyl)-2-(4-morpholino)-acetonitrile; m.p. 160°–161° C.

EXAMPLE 11

Analogously to Example 10 are obtained:

| Name | Yield % | melting point °C. (solvent) |
|---|---|---|
| (1) 4,5-Dihydro-6-[2-(4-pyridyl-amino)-5-pyridyl]-3(2H)-pyridazinone | 62 | 287–89 $CH_3OH$ |
| (2) 4,5-Dihydro-5-methyl-[2-(4-pyridylamino)-5-pyridyl]-3-(2H)pyridazinone | 55 | 221–23 ($CH_3OH$) |
| (3) 4,5-Dihydro-6-[2-(thiazolylamino)-5-pyridyl]-3-(2H)-pyridazinone | 48 | 275–77 (EtOH) |

We claim:

1. Pyridazinone derivative of the formula:

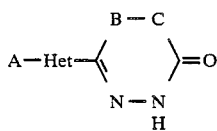 (I)

wherein
Het is a mono- or bicyclic heterocycle selected from the group consisting of pyridine, pyrazine, pyrimidine, pyridazine, quinoline, isoquinoline, quinoxaline, quinazoline and phthalazine,
B-C is a —$CHR_1$—$CH_2$— or —$CR_1$=CH— group $R_1$ being a hydrogen atom or a lower alkyl radical, and
A is an amino, lower alkylcarbonylamino, aminocarbonylamino, aminothiocarbonylamino, lower alkylaminothiocarbonylamino, lower alkylaminocarbonylamino, N'-cyanoguanidino or N'-cyano-N''-lower alkylguanidino group, or a group of the formula X-Y, wherein Y is —NH— or 13 S— and X is phenyl or a heterocyclic ring selected from the group consisting of pyridyl, thiazole, triazole, and tetrazole, with the phenyl ring and the heterocyclic ring being unsubstituted or containing at least one substituent selected from the group consisting of $C_1$-$C_6$ alkyl, $C_1$-$C_6$ alkoxy, hydroxyl, nitro or halogen, or A is a mono- or bicyclic heterocycle selected from the group consisting of pyrrole, pyrazole, piperidine, piperazine, triazine, benzimidazole and 4,5,6,7-tetrahydrobenzimidazole, with the said heterocycle being unsubstituted or containing at least one substituted selected from the group consisting of $C_1$-$C_6$ alkyl, $C_1$-$C_6$ alkoxy, hydroxyl, ($C_1$-$C_6$ alkyl) carbonylamino;
and the physiologically acceptable salts thereof.

2. Derivative of claim 1, wherein
Het is selected from the group consisting of pyridine, pyrazine, pyrimidine, pyridazine and phthalazine,
B-C is selected from the group consisting of —$CHR'_1$—$CH_2$ and —$CR'0_1$=CH— groups, wherein $R'_1$ is a hydrogen atom or a methyl radical and
A is selected from the group consisting of lower alkylcarbonylamino, aminocarbonylamino, aminothiocarbonylamino, lower alkylaminocarbonylamino, N'-cyano-N''-lower alkylguanidine, amino, phenylamino, thiazoleamino, pyridylamino, tetrazoleamino or triazolethio radicals, wherein the phenyl ring and the heterocyclic rings contain no substituent or are substituted with at least one substituent selected from the group consisting of methyl, methoxy, hydroxyl, and chlorom or A is selected from the group consisting of pyrrole, pyrazole, piperidine, piperazine, triazine, benzimidazole, and tetrahydrobenzimidazole, which are unsubstituted or are substituted by at least one substituent selected from the group consisting of methyl, hydroxyl, methylcarbonyl and methylcarbonylamino,
and the physiologically acceptable salts thereof.

3. Derivative of claim 1 or 2, wherein
Het is a pyridine ring, $R_1$ is a hydrogen atom or a methyl radical, and
A is lower alkylcarbonylamino, lower alkylaminocarbonylamino, phenylamino, pyridylamino, thiazoleamino, pyrrole, benzimidazole or tetrahydrobenzimidazole and the physiologically acceptable salts thereof.

4. Derivative of claim 1, wherein B-C is —$CHR'_1$—$CH_2$— or —$CR'_1$=CH—, wherein $R_1$ is a hydrogen atom or $C_{1-3}$ alkyl.

5. A compound selected from the group consisting of:
4,5-dihydro-6-[2-(4-pyridyl-amino)-5-pyridyl]-3(2H)-pyridazinone;
4,5-dihydro-5-methyl-[2-(4-pyridylamino)-5-pyridyl]-3-(2H)-pyridazinone; and
4,5-dihydro-6-[2(thia-zolylamino)-5-pyridyl]-3-(2H)-pyridazinone.

6. Derivative of claim 1, wherein A is amino, ($C_1$-$C_5$ alkyl)-carbonylamino, ($C_1$-$C_5$ alkyl)aminocarbonylamino, or N'-cyano-N''-($C_1$-$C_5$ alkyl)-guanidino, aminocarbonylamino, or aminothiocarbonylamino.

7. Derivative of claim 1, wherein A is selected from the group consisting of phenylamino, pyridylamino, thiazoleamino, tetrazoleamino, phenylthio, pyridylthio, thiazolethio, triazolethio, and tetrazolethio which are unsubstituted or substituted by at least one member selected from the group consisting of $C_1$-$C_6$ alkyl, $C_1$-$C_6$ alkoxy, hydroxyl, nitro or halogen.

8. Derivative of claim 1, wherein said derivative is 4,5-dihydro-5-methyl-6-[2-(1H-benzimidazol-1-yl)-5-pyridyl]-3(2H)-pyridazinone.

9. Derivative of claim 1, wherein said derivative is 4,5-dihydro-5-methyl-6-[2-methylaminocarbonylamino)-5-pyridyl]-3(2H)-pyridazinone.

10. Derivative of claim 1, wherein said derivative is 4,5-dihydro-5-methyl-6-[2-(1-pyrrolyl)-5-pyridyl]-3(2H)-pyridazinone.

11. Derivative of claim 1 wherein, wherein said derivative is 4,5-dihydro-5-methyl-6-[2-(phenylamino)-5-pyridyl]-3(2H)-pyridazinone.

12. Pharmaceutical composition for treating heart and circulatory disease, comprising an effective amount of a compound of claim 12 and a pharmaceutically acceptable carrier or diluent.

13. Composition of claim 12, wherein said composition is in the form of a tablet containing 0.5 to 20 mg of said compound.

14. Method of reducing blood pressure in a patient in need of such reduction, said method comprising administering to said patient an effective amount of a compound of claim 2.

15. Method of producing a positive isotropic action in a patient in need of such action, said method comprising administering to said patient an effective amount of a compound of claim 2.

16. A method of influencing thrombocyte aggregation in a patient in need of such influence, said method comprising administering to said patient an effective amount of a compound of claim 1.

17. A method of improving microcirculation in a patient in need of such improvement, said method comprising administering to said patient an effective amount of a compounf of claim 2.

18. Method of claim 14, wherein said amount is about 1 to 50 mg per day.

19. Method of claim 15, wherein said amount is about 1 to 50 mg per day.

20. Method of claim 16, wherein said amount is about 1 to 50 mg per day.

21. Method of claim 17, wherein said amount is about 1 to 50 mg per day.

* * * * *